United States Patent [19]

Clark et al.

[11] Patent Number: 6,103,245
[45] Date of Patent: Aug. 15, 2000

[54] TOPICAL BARRIER COMPOSITION CONTAINING SILICONE AND BENTONITE

[75] Inventors: Mary G. Clark, Clarks Summit; Robert P. Digiovine, Gouldsboro, both of Pa.

[73] Assignee: Derma Sciences, Inc., Wilkes-Barre, Pa.

[21] Appl. No.: 08/967,276

[22] Filed: Nov. 7, 1997

Related U.S. Application Data

[63] Continuation of application No. 08/652,022, May 21, 1996.

[51] Int. Cl.⁷ .............................. A61K 7/00; A61K 6/00; A61K 7/34; A61K 31/74
[52] U.S. Cl. .................... 424/401; 424/66; 424/78.07; 424/59
[58] Field of Search ................ 426/401, 59, 66, 426/78.07

[56] References Cited

U.S. PATENT DOCUMENTS 4,559,157  12/1985  Smith et al. ................ 252/90
4,917,891   4/1990  Kaufmann et al. ........... 424/401
5,776,917   7/1998  Blank et al. ................. 514/159

OTHER PUBLICATIONS

Muller–Goymann, C.C.; New Expedient Substances in the Preparation of Dermatological and Cosmetic Products; AN 92331104 EMBASE abstract:, 1992.

Figueroa, Jr., USPATFULL abstract AN 90: 76704, abstract of US 4960764, Oct. 1990.

*Primary Examiner*—John Kight
*Assistant Examiner*—D. Faulkner
*Attorney, Agent, or Firm*—Shook, Hardy & Bacon L.L.P.

[57] ABSTRACT

A topical barrier composition contains a, synthetic, polymeric, hydrophobic silicone material, a bentonite component, zinc oxide, water and an unctuous carrier base for the other ingredients of the composition. The composition provides a barrier function protecting mammalian epidermis against external insults such as hyperhydration and maceration from any cause with an intended use for protection against extended periods of exposure to urine and feces.

28 Claims, No Drawings

TOPICAL BARRIER COMPOSITION CONTAINING SILICONE AND BENTONITE

This application is a continuation of copending application Ser. No. 08/652,022 filed on May 21, 1996.

FIELD OF THE INVENTION

The present invention relates to the field of barrier compositions for use in protecting human or animal tissues, especially epithelial tissues, from contact with external agents. In particular the invention provides a topical barrier cream containing a silicone material, a bentonite component and an unctuous carrier base.

BACKGROUND OF THE INVENTION

Barrier compositions and creams are well known in the art. In connection with such compositions and creams there is a continuum of activities directed to improving product characteristics. Much effort is directed to the improvement of product substantivity on skin surfaces. Compositions are sought which have expanded utility such that the composition may be used generally in a multiplicity of applications. For example, barrier creams and compositions have application as hand creams, lip balm, facial cosmetics, diaper creams, ostomic creams, medicinal creams, and the like. In sum, desirable preparations possess many positive characteristics including superior water repellency, resistance to being washed off, physiological mildness, and a pleasant feel which enhances user comfort and compliance. Ideally, a barrier cream should be smooth and silky as opposed to tacky or sticky. Moreover, the ideal composition should possess a maximum number of beneficial characteristics.

SUMMARY OF THE INVENTION

The present invention relates to a novel topical barrier composition which comprises a synthetic, polymeric, hydrophobic silicone material, a bentonite component, and an unctuous carrier base for the ingredients of the composition. In accordance with the invention, the novel composition of the present invention provides a barrier cream which is smoother than many known barrier compositions. It has been found that the composition of the invention is not as greasy as other barrier creams and its characteristics are such that it does not interfere with diaper or underpad function. The novel combination of ingredients provided by the present invention results in a product having an ability to retain aqueous solutions rather than allowing them to come into contact with unprotected skin. The novel composition of the invention has also been found to act as a barrier to both aqueous solutions and organic mixtures. The composition results in a creamy formulation which possesses substantial adhesion to the skin thereby providing prolonged staying ability. The novel ingredients provide a product which resists dissolution. As a result of the combined properties of adhesion to the skin and resistance to dissolution, the composition of the invention provides an effective barrier in the event of back-to-back episodes of incontinence in which a patient has not been attended to after the first episode. Importantly, the composition of the invention generally includes no nutrients which might support the growth of bacteria. Moreover, the bentonite in the composition of the invention exhibits a property of microbial adsorption to further control bacterial presence and growth. In addition, the composition of the present invention does not need to contain synthetic dyes or fragrances which might be irritating to sensitive skin.

The composition of the invention provides a superior, longer-lasting barrier cream for incontinent patients. Additionally, the composition is known to prevent diaper rash and has a prolonged staying ability. On the other hand, the composition of the invention does not interfere with normal diaper function and does not contain any ingredients which might irritate sensitive skin. Furthermore, the composition of the invention provides an effective sunscreening mechanism and has the ability to remain on the skin during swimming or rather vigorous exercise. The composition of the invention aids in the retention of the natural moisture of human skin even when the host is exposed to hot sun or warm breezes. The barrier composition of the invention is an effective skin protective product which might serve as a second barrier in addition to the protection provided by gloves. Thus, in the event that the protective barrier offered by gloves should be compromised, the composition presents a secondary, temporary barrier to protect the hands. The composition also provides an effective barrier against aqueous solutions and mixtures as well as many organic solvents.

The topical barrier composition of the invention provides an effective barrier to prevent the loss of moisture from the skin. Workers exposed to heat, wind (or high air flow), liquid precipitation or salt water spray may protect themselves by applying the composition to exposed skin. Also, the composition of the invention provides an effective hand cream to prevent water loss due to handling of materials which acts as desiccants, for example, dried lumber, polishing compounds, etc.

The composition of the invention also provides a superior base for smear-free cosmetics. The silicone materials present in the composition are effective to prevent the dissolution of cosmetic formulations by moisture and the ingredients of the composition generally permit the incorporation therein of a wide variety of additional cosmetic ingredients. By carefully adjusting the pH level of the composition, a long-lasting protective barrier to aid in wound healing is provided.

As set forth above, the present invention provides a topical barrier composition comprising a silicone material, a bentonite component and an unctuous carrier base. Preferably the silicone material in the composition has an initial viscosity before incorporation into the composition within the range of from about $10^2$ to about $10^8$ centistokes at 25° C. Ideally, the composition of the invention may also include an inorganic compound, preferably a zinc oxide component, serving as a barrier between human skin and external aqueous materials. Alternatively the inorganic barrier material may be aluminum hydroxide, magnesium silicate, titanium dioxide, kaolin, zinc acetate, zinc carbonate, zinc stearate, calamine, talc, etc. In accordance with the preferred aspects of the invention, the inorganic barrier component may be micronized to particle size such that the topical barrier composition is smooth and homogenous and has an essentially grit free constituency. Specifically, the composition may contain from about 1 to about 75 parts by weight of the unctuous carrier base, from about 0.005 to about 70 parts by weight of the silicone material, from about 0.005 to about 50 parts by weight of the bentonite component, and from about 1 to about 40 parts by weight of the inorganic compound component.

From a practical view point, the silicone material present in the topical barrier composition of the invention may comprise a silicone, a siloxane or a polysiloxane. Preferably, the polysiloxane may be a linear polysiloxane, a branch-chain, polysiloxane, an alkyl polysiloxane, or a hydroxy terminated dialkyl polysiloxane. Ideally, the silicone material may comprise a dimethylpolysiloxane.

The topical barrier composition of the invention may comprise a homogenous, smooth cream which is essentially free of lumps and particulate matter and preferably has a pH within the range of from about 2.0 to about 10.0. Ideally, the composition has a pH within the range of from about 5.4 to about 7.4.

The topical barrier composition of the invention may include a sufficient amount of water to form a gel with the bentonite component.

In one form of the invention, the hydrophobic silicone material of the topical barrier composition of the invention may comprise a cyclomethicone, dimethiconol, dimethicone, or phenyltrimethicone.

DESCRIPTION OF THE PREFERRED EMBODIMENTS

Generally speaking, the invention provides a topical barrier composition which comprises a synthetic, polymeric, hydrophobic silicone material, a bentonite component, and an unctuous carrier base for the ingredients of the composition. The bentonite component generally consists of a mixture of inorganic salts which serve as an emulsifier for aqueous and oil phases. Additionally, bentonite forms gels with water, which gives compositions containing bentonite an ability to retain aqueous solutions. Bentonite also exhibits microbial adsorption characteristics for hygienic purposes.

The unctuous carrier base may comprise a white petrolatum material which also serves as a barrier between the skin and external aqueous solutions and mixtures. Preferably, the silicone material may ideally comprise dimethiconol which has talc-like characteristics and tends to remain on the skin as a lasting barrier.

In a particularly preferred form of the invention, a topical barrier composition having the following formulation is provided:

| | |
|---|---|
| Sodium Chloride | 1.00% by weight |
| Magnesium Sulfate | 1.00% by weight |
| Methylparaben | 0.075% by weight |
| Propylparaben | 0.015% by weight |
| Purified water | 23.34% by weight |
| Bentontonite | 5.25% by weight |
| White petrolatum | 40.00% by weight |
| Dow Corning Q2-5200 | 2.00% by weight |
| Span 60 | 2.00% by weight |
| Brij 78 | 0.30% by weight |
| Dow Corning 1401 | 5.00% by weight |
| Zinc oxide | 20.00% by weight |
| Vitamin A Palmitate | 0.02% by weight |

The specified concentrations of methylparaben and propylparaben in the preferred formulation are the highest concentrations of the parabens which can be dissolved in the quantity of water containing the concentrations of sodium chloride and magnesium sulfate used in the formulation at 70° C. In order to increase the propylparaben concentration to as much as 0.02 weight percent, the temperature of the aqueous phase during its preparation would have to be about 70° C. In order to obtain the paraben concentrations set forth in the foregoing formulation, the aqueous phase must be stirred at about 70° C. until all of the solids are dissolved and a clear solution as obtained. It should be noted in this regard that the inorganic salt concentrations set forth in the above formulation are based on the weight of anhydrous salt used in the formulation. The purified water should have an initial pH between about 5.40 and 6.00. If the pH of the water is not already in this range, the pH may be adjusted with hydrochloric acid or sodium hydroxide.

In preparing the barrier cream of the formulation set forth above, two phases are prepared. The first phase includes the white petrolatum, the Dow Corning Q2-5200 (formulation aid) and Brij 78. These materials are combined and the mixture is heated with stirring to a temperature of 70° C. The second phase includes the sodium chloride, the magnesium sulfate, the methylparaben, the propylparaben and the purified water. These ingredients are mixed and heated with stirring to 70° C. to provide a clear aqueous solution. The bentonite is sprinkled into the resulting second phase aqueous solution with stirring. The completed second phase is a smooth lump-free suspension. The two phases are added together slowly using a high shear apparatus such as a hydro-shear, homomixer or colloid mill. It is important to slowly add the second phase to the first phase. The process may be started by adding approximately 1 percent of the second phase to the first phase and then mixing with high turbulence until a uniform mixture is obtained. The remaining second phase is then added to the first phase very slowly and steadily with high turbulence. When all of the second phase has been added, stirring is continued with high turbulence for approximately 30 minutes while the mixture remains at a temperature of about 70 to about 75° C. The resultant emulsion may then be cooled to between about 55 to 58° C. while stirring is continued. The Dow 1401 ingredient is added to the emulsion while turbulent stirring is continued and while maintaining the temperature of the emulsion near 55° C. The Dow 1401 material is added slowly and steadily to the emulsion. Turbulent stirring of the resulting emulsion is then continued for another 30 minutes or so while the temperature is maintained at about 55° C.

At this point the zinc oxide ingredient is sprinkled on to the top of the resulting emulsion while turbulent stirring with a high shear mixer is continued. During this zinc oxide addition, the temperature of the emulsion is maintained at about 55° C. Stirring of the resultant mixture is continued for another 30 minutes or so at about 55° C.

At this point the emulsion is cooled to about 33 to about 38° C. while stirring continued. Then the vitamin A component is added while stirring is continued at a temperature of 33 to 38° C. for another 15 minutes or so.

The topical barrier composition which is the subject matter of the present invention may be used for protection of mammalian epidermis against external insults that may result from exposure to thermal, biological, chemical, occupational and/or environmental stimuli (i.e., moisture, wind, solar (UV), and visible light, etc.). In addition, the barrier composition of the invention will prevent moisture loss from skin without compromising the natural acid skin mantle, thus permitting natural healing processes to progress for inflammatory and partial thickness abnormalities associated with the epithelial layers of the skin. The novel composition provides a superior long lasting barrier formulation with an intended use as a protective barrier for incontinent patients along with use for managing diaper rash in humans. Additional uses include any skin protection required for persons exposed to excessive periods of thermal, biological, chemical, occupational and/or environmental stimuli such as has been described above. The composition also provides a vehicle base for smear free cosmetics.

In its broadest sense, the composition of the invention contains a synthetic, polymeric, hydrophobic silicone material, bentonite and an unctuous carrier base such as petrolatum. Generally speaking, the composition may also include an inorganic barrier component and water. By manipulating the concentrations of the ingredients in a manner well known to those of ordinary skill in the art to which the invention pertains, the composition may be formulated into products ranging from liquid to solid dosage forms. Primarily the composition provides a formulation which will protect mammalian epidermis against external insults such as hyperhydration and maceration from any cause with an intended use for protection against extended periods of exposure to urine and feces.

Broadly, the composition may be formulated so as to provide a pH within the range of from about 2.0 to about 10.0. optimally, the preferred formulations including the composition of the invention may have a pH within the range of from about 5.4 to about 7.4.

The unctuous carrier base for the composition of the invention may generally be a white petrolatum material. White petrolatum may sometimes be referred to as a white petroleum jelly or white soft paraffin. In particular, the material consists of a purified mixture of semisolid hydrocarbons obtained from petroleum which has been wholly or nearly decolorized. Often it may contain a stabilizer. This material may be described as being a white or faintly yellowish, unctuous mass which is transparent in thin layers, even after cooling to 0° C. Generally the petrolatum has a specific gravity of from 0.815 to 0.880 at 60° C. and melts at a temperature between 38 and 60° C.

While white petrolatum is the preferred material for use as the unctuous carrier base in the composition of the invention, other petrolatums and/or light mineral oils also may be used in accordance with the concepts of the invention. And the unctuous carrier base may be present in the composition in amounts ranging from about 1 weight percent to about 75 weight percent based on the total weight of the overall composition.

The particularly preferred unctuous carrier base material for use in accordance with the present invention comprises a material known as Penreco snow white petrolatum USP produced by Penreco Company of Karns City, Pa.

The preferred synthetic, polymeric, hydrophobic silicone material useful in accordance with the preferred embodiments of the invention consists of a high molecular weight, non-volatile, ultra-high viscosity dimethiconol polymer (dimethyl polysiloxane). This material is fully described in U.S. Pat. No. 4,152,416, the entirety of the disclosure of which is incorporated herein by reference. Preferably, the dimethiconol utilized for purposes of the present invention will be incorporated into the composition as a mixture of the dimethiconol ingredient with a cyclomethicone. Such a mixture is available commercially under the name of Dow Corning 1401 fluid. The Dow Corning 1401 fluid is a blend of ultra-viscosity dimethiconol (13% by weight) and a volatile cyclomethicone fluid. The dimethiconol ingredient exhibits increases in substantivity in proportion to increasing molecular weight.

The cyclomethicone ingredient is utilized as a carrier to deliver the high molecular weight dimethiconol. The combination of a volatile silicone and a high molecular weight non-volatile, substantive silicone initially provide the same benefits of dimethiconol that are typical of the personal care industry. The cyclomethicone ingredient is an ideal carrier for the dimethiconol since it provides excellent application and spreading characteristics and has an excellent tactile feel. After its function as a carrier is complete, the cyclomethicone rapidly evaporates without cooling the skin and the dry (talc-like) feel of the dimethiconol is the result.

The silicone material may be present in the composition in amounts ranging from about 0.005 to about 70 weight percent of the overall composition. Preferably, however, the composition may include between about 0.1 and about 1.0 weight percent of the silicone composition.

The silicone ingredient contained in the barrier composition preferably may be a substantive silicone which has solid quality, substantial character, consistency and body. That is to say, the silicone ingredient provides substance for the barrier composition. The silicone ingredient improves the body, texture, consistency and aesthetics of the invention as a result of its desired substantive nature. Thus, the silicone ingredient improves the texture and feel of the composition while eliminating undesirable greasiness.

In accordance with the invention, the silicone component that is useful in accordance with the present invention may be a silicone, a siloxane, a polysiloxane, a straight-chain polysiloxane, an alkyl polysiloxane, dimethiconol or a hydroxyterminated dimethylpolysiloxane. More particularly, the silicone ingredient may be cyclomethicone, dimethiconol, dimethicone, or phenyltrimethicone. In any event, the silicone component should have a viscosity within the range of from about $10^2$ to about $10^8$ centistokes at 25° C. Functionally, the viscosity of the silicone ingredient should be sufficient to provide substantive properties to the overall composition.

The bentonite ingredient may be present in the composition in amounts ranging from about 0.0005 to about 50 weight percent of the total weight of the overall composition. Bentonite, which is sometimes known as Wilhinite, soap clay or mineral soap, is a native, colloidal, hydrated aluminum silicate. This material is known to be a protective colloid for the stabilization of suspensions. It has also been used as an emulsifier for oil and as a base for plasters, ointments and similar preparations. In the composition of the present invention, bentonite serves as an emulsifier for the aqueous phase and the oil phase. Also, the bentonite forms gels with water to give the barrier composition an ability to retain aqueous solutions. Bentonite also is capable of microbial adsorption which may tend to inhibit microbial activity. In the preferred form of the invention, the bentonite which is useful in accordance with the invention is known as 670 bentonite NF BC, a product which is obtainable from Whittaker, Clark and Daniels, Inc. of South Plainfield, N.J.

In accordance with the preferred aspects of the invention, the bentonite may be present in the formulation in an amount ranging from about 3.5 to about 7 weight percent.

Sodium chloride and magnesium sulfate are used in the preferred form of the invention to increase the ionic strength of the aqueous phase. The presence of such electrolytes in the aqueous phase helps to stabilize the water/silicone emulsion. Such salts may or may not be present in the composition of the invention.

Methylparaben and propylparaben are used as a preservative system for the product. Once again, preservatives may or may not be present in the composition.

The Dow Q2-5200 component of the preferred composition is a laurylmethicone copolyol. This material is used as a formulation aid to aid in the formation of a stable emulsion of the aqueous phase and the silicone phase. Once again, this ingredient may or may not be present in the composition of the invention. The Brij 78 ingredient of the preferred composition is a polyoxyethylene (20) stearyl ether which serves as a non-ionic surfactant. This material acts as an emulsifier to lower the surface tension of the composition while the aqueous phase and the oil phase are being combined. This allows the aqueous phase and the oil phase to form a stable emulsion. Such materials are well known to those of ordinary skill in the art and may or may not be included in the composition of the invention.

The inorganic barrier component, which preferably may be zinc oxide, should be micronized to a particle size such that the barrier composition itself, after the addition of the inorganic component, is a smooth homogenous composition that is essentially grit free. The preferred zinc oxide material is a very fine, odorless, amorphous, white or yellowish white powder which is free from gritty particles. Zinc oxide has a mild astringent, protective and antiseptic action. Thus, it is often used in the treatment of dry skin and such skin disorders and a number of epidermal infections. The inorganic barrier component may be present in the composition in a range of from about 1 to about 40 percent by weight. More preferably the inorganic barrier component may be present in an amount ranging from about 15 to about 25 percent by weight. Other suitable materials which may be used instead of the zinc oxide, or in addition thereto, include inorganic compounds such as aluminum hydroxide, magnesium silicate, titanium dioxide, kaolin, zinc acetate, zinc carbonate, zinc stearate, calamine, talc, etc.

Vitamin A is included in the preferred formulation because of its anti-oxidant properties.

The water ingredient provides a volatile solvent for the inorganic components of the composition.

The barrier composition of the invention offers maximum barrier effectiveness and long lasting barrier effect. The composition provides a smooth, non-greasy substantive formulation having hygroscopic properties for holding moisture in place. The composition adheres readily to skin and has excellent resistance to dissolution. The formulation impedes bacterial growth, contains no synthetic dyes or fragrances and has a bio-compatible pH.

The composition provides maximum substantive skin protection when applied on a once daily basis. The material is smooth and therefore easy to apply, and after application prevents moisture run off to unaffected skin. When used to inhibit diaper rash, the composition leaves no residual materials on the diaper and therefore protects skin more effectively. The composition does not wash off with water or urine, although it is removable with soap and water. The formulation supports a natural acid mantle of the skin and provides excellent protective benefits.

We claim:

1. A substantive, dissolution resistant topical barrier composition comprising at least three different principal ingredient materials including (a) a non-volatile, synthetic, polymeric, hydrophobic silicone material, (b) a bentonite component, and (c) an unctuous carrier base for the other ingredients of the composition.

2. A topical barrier composition as set forth in claim 1, wherein said silicone material has an initial viscosity before incorporation into said composition within the range of from about $10^2$ to about $10^8$ centistokes at 25° C.

3. A topical barrier composition as set forth in claim 1, wherein said composition includes a zinc oxide component.

4. A topical barrier composition as set forth in claim 1, wherein said composition contains from about 1 to about 75 parts by weight of said unctuous carrier base, from about 0.0005 to about 70 parts by weight of said silicone material, and from about 0.0005 to about 50 parts by weight of said bentonite component.

5. A topical barrier composition as set forth in claim 3, wherein said composition contains from about 1 to about 75 parts by weight of said unctuous carrier base, from about 0.0005 to about 70 parts by weight of said silicone material, from about 0.0005 to about 50 parts by weight of said bentonite component, and from about 1 to about 40 parts by weight of said zinc oxide component.

6. A topical barrier composition as set forth in claim 1, wherein said silicone material comprises a silicone, a siloxane, or a polysiloxane.

7. A topical barrier composition as set forth in claim 6, wherein said polysiloxane comprises a linear polysiloxane, a branched-chain polysiloxane, an alkyl polysiloxane, or a hydroxy terminated dialkyl polysiloxane.

8. A topical barrier composition as set forth in claim 7, wherein said alkyl polysiloxane comprises a dimethyl polysiloxane.

9. A topical barrier composition as set forth in claim 3, wherein said silicone material comprises a silicone, a siloxane, or a polysiloxane.

10. A topical barrier composition as set forth in claim 9, wherein said polysiloxane comprises a linear polysiloxane, a branched-chain polysiloxane, an alkyl polysiloxane, or a hydroxy terminated dialkyl polysiloxane.

11. A topical barrier composition as set forth in claim 10, wherein said alkyl polysiloxane comprises a dimethyl polysiloxane.

12. A topical barrier composition as set forth in claim 3, wherein said silicone material has an initial viscosity before incorporation into said composition within the range of from about $10^2$ to about $10^8$ centistokes at 25° C.

13. A topical barrier composition as set forth in claim 1, wherein said composition comprises a homogenous, smooth cream.

14. A topical barrier composition as set forth in claim 3, wherein said composition comprises a homogenous, smooth cream.

15. A topical barrier composition as set forth in claim 1, wherein said composition has a pH within the range of from about 2.0 to about 10.0.

16. A topical barrier composition as set forth in claim 15, wherein said composition has a pH within the range of from about 5.4 to about 7.4.

17. A topical barrier composition as set forth in claim 3, wherein said composition has a pH within the range of from about 2.0 to about 10.0.

18. A topical barrier composition as set forth in claim 17, wherein said composition has a pH within the range of from about 5.4 to about 7.4.

19. A topical barrier composition as set forth in claim 1, wherein said composition includes an inorganic compound serving as a barrier between human skin and external aqueous materials.

20. A topical barrier composition as set forth in claim 19, wherein said inorganic compound has been micronized to reduce the particle size to such a point that the topical barrier composition comprises a homogenous, smooth cream.

21. A topical barrier composition as set forth in claim 19, wherein said inorganic compound comprises zinc oxide, aluminum hydroxide, magnesium silicate, titanium dioxide, kaolin, zinc acetate, zinc carbonate, zinc stearate, calamine or talc.

22. A topical barrier composition as set forth in claim 21, wherein said inorganic compound has been micronized to reduce the particle size to such point that the topical barrier composition comprises a homogenous, smooth cream.

23. A topical barrier composition as set forth in claim 1, wherein said composition includes a sufficient amount of water to form a gel with said bentonite component.

24. A topical barrier composition as set forth in claim 3, wherein said composition includes a sufficient amount of water to form a gel with said bentonite component.

25. A topical barrier composition as set forth in claim 1, wherein said hydrophobic silicone material comprises a cyclomethicone, dimethiconol, dimethicone, or phenyltrimethicone.

26. A topical barrier composition as set forth in claim 3, wherein said hydrophobic silicone material comprises a cyclomethicone, dimethiconol, dimethicone, or phenyltrimethicone.

27. A topical barrier composition as set forth in claim 3, wherein said zinc oxide component has been micronized to reduce the particle size to such point that the topical barrier composition comprises a homogenous, smooth cream.

28. A substantive, dissolution resistant topical barrier composition having the following formulation:

| | |
|---|---|
| Sodium Chloride | 1.00% by weight |
| Magnesium Sulfate | 1.00% by weight |
| Methylparaben | 0.075% by weight |
| Propylparaben | 0.015% by weight |
| Purified water | 23.34% by weight |
| Bentontonite | 5.25% by weight |
| White petrolatum | 40.00% by weight |
| Dow Corning Q2-5200 | 2.00% by weight |
| Span 60 | 2.00% by weight |
| Brij 78 | 0.30% by weight |
| Dow Corning 1401 | 5.00% by weight |
| Zinc oxide | 20.00% by weight |
| Vitamin A Palmitate | 0.02% by weight. |

* * * * *